(12) United States Patent
Lee et al.

(10) Patent No.: US 11,464,445 B2
(45) Date of Patent: Oct. 11, 2022

(54) DATA PROCESSING APPARATUS FOR AUTOMATICALLY DETERMINING SLEEP DISORDER USING DEEP LEARNING AND OPERATION METHOD OF THE DATA PROCESSING APPARATUS

(71) Applicant: HONEYNAPS CO., LTD., Seoul (KR)

(72) Inventors: Young Jun Lee, Seoul (KR); Tae Kyoung Ha, Seoul (KR)

(73) Assignee: HONEYNAPS CO., LTD., Seoul (KR)

( * ) Notice: Subject to any disclaimer, the term of this patent is extended or adjusted under 35 U.S.C. 154(b) by 110 days.

(21) Appl. No.: 16/744,331

(22) Filed: Jan. 16, 2020

(65) Prior Publication Data
US 2021/0045675 A1    Feb. 18, 2021

(30) Foreign Application Priority Data

Aug. 12, 2019  (KR) .......................... 10-2019-0098257

(51) Int. Cl.
*A61B 5/00* (2006.01)
*A61B 5/369* (2021.01)
(Continued)

(52) U.S. Cl.
CPC ............ *A61B 5/4812* (2013.01); *A61B 5/369* (2021.01); *A61B 5/389* (2021.01); *A61B 5/398* (2021.01)

(58) Field of Classification Search
CPC ....... A61B 5/4812; A61B 5/369; A61B 5/389; A61B 5/398; A61B 5/7267; A61B 5/4806;
(Continued)

(56) References Cited

U.S. PATENT DOCUMENTS

2007/0167858 A1\* 7/2007 Virtanen .................. A61B 5/30
600/544
2015/0126821 A1\* 5/2015 Kempfner ............ A61B 5/4809
600/301
(Continued)

FOREIGN PATENT DOCUMENTS

JP          2019-509151 A    4/2019
KR   10-2012-0012364 A1    2/2012
(Continued)

OTHER PUBLICATIONS

"A simple format for exchange of digitized polygraphic recordings" Bob Kemp a Alpo Varri b, Agostinho C. Rosa c, Kim D Nielsen d and John Gade Electroencephalography and clinical Neurophysiology , 82 (1992) 391-393 (Year: 1992).\*
"Interpolation and Decimation of Digital Signals a Tutorial Review" Ronald E. Crochiere, Proceedings of the IEEE, vol. 69, No. 3, Mar. 1981 (Year: 1981).\*
Communication dated Oct. 29, 2020 by the Korean Patent Office in application No. 10-2019-0098257.

*Primary Examiner* — Brian T Gedeon
*Assistant Examiner* — Joshua Andrew Schum-Houck
(74) *Attorney, Agent, or Firm* — Sughrue Mion, PLLC

(57) ABSTRACT

Provided is a data processing apparatus including a signal data processor configured to collect signal data detected through polysomnography, to extract feature data by analyzing a feature of the collected signal data, and to transform the extracted feature data to time series data; and a sleep stage classification model processor configured to input the processed signal data to a pre-generated sleep stage classification model, and to classify a sleep stage corresponding to the signal data. The signal data processor is configured to extract feature data by analyzing a feature of each of an electroencephalographic (EEG) signal, an electro-oculographic (EOG) signal, and an electromyographic (EMG) signal with respect to the signal data, and to transform the extracted feature data to an epoch unit of time series data to
(Continued)

input the extracted feature data to the pre-generated sleep stage classification model.

7 Claims, 5 Drawing Sheets

(51) Int. Cl.
*A61B 5/389* (2021.01)
*A61B 5/398* (2021.01)

(58) Field of Classification Search
CPC .... A61B 5/7264; A61B 5/7275; G16H 40/63; G16H 50/00
See application file for complete search history.

(56) References Cited

U.S. PATENT DOCUMENTS

2017/0215808 A1* 8/2017 Shimoi ................ A61B 5/0205
2019/0192069 A1* 6/2019 Garcia Molina .... A61B 5/4812

FOREIGN PATENT DOCUMENTS

KR 10-1395197 B 5/2014
WO WO-2018070935 A1 * 4/2018 ............. G16H 50/20

\* cited by examiner

DATA PROCESSING APPARATUS FOR AUTOMATICALLY DETERMINING SLEEP DISORDER USING DEEP LEARNING AND OPERATION METHOD OF THE DATA PROCESSING APPARATUS

CROSS-REFERENCE TO RELATED APPLICATION

This application claims priority from and the benefit of Korean Patent Application No. 10-2019-0098257 filed on Aug. 12, 2019, which is hereby incorporated by reference in its entirety.

BACKGROUND

1. Field

The following description of example embodiments relates to a data processing apparatus for automatically determining a sleep disorder using a deep learning and an operation method of the data processing apparatus, and more particularly, to a technical spirit for automating a result analysis of polysomnography.

2. Related Art

Polysomnography refers to a test for diagnosing a sleep disorder and is used to diagnose a sleep-related disorder and to determine a treatment method by collectively measuring a brain wave, an electrooculogram (eye movement), a movement of muscle, a respiration, an electrocardiogram (ECG), etc., during sleep, and, at the same time, videotaping a sleep state and then analyzing a videotaped recording.

The aforementioned polysomnography may diagnose symptoms, for example, sleep apnea, a sleep disorder, sleepwalking, etc. As an index for determining such disorder, a sleep stage, an apnea-hypopnea index (AHI), a respiratory effort-related arousals (RERA) index, and the like are used.

Meanwhile, polysomnography employs a manual sleep scoring method that determines the aforementioned indices by combining biometric data of a patient measured using various sensors by experts.

That is, current polysomnography proceeds with sleep scoring based on a subjective determination standard of each expert. Therefore, accuracy and reliability of a scoring result may be degraded.

In detail, in polysomnography, although a determination standard for sleep scoring appears to be very clear, a shape or a magnitude of a biosignal differs for each patient and many errors occur even among experts due to an irregularly appearing biosignal. In reality, when experts run sleep scoring using the same biometric data of the same patient, a scoring deviation of about 20% occurs.

Further, since sleep scoring is performed through a manual operation by an expert, a relatively large amount of time is used. For example, it may take about 3 or 4 hours for a skilled expert to run sleep scoring on a single patient.

Electroencephalogram (EEG) is a biosignal monitoring apparatus generally used to analyze a sleep stage of a patient to diagnose a sleep disorder, such as insomnia and narcolepsy. In addition, the sleep stage may be determined by accessorily using electrooculogram (EOG) and chin-electromyogram (EMG).

In general, a procedure of determining a sleep disorder, such as insomnia, may follow as:

1) In general, EEG, EOG, and chin-EMG may be measured during sleep of predetermined hours in a hospital equipped with a polysomnography center.

2) A qualified technician derives a result by manually performing a sleep stage analysis on a measured result under supervision of a sleep specialist.

3) A sleep specialist diagnoses a sleep disorder based on the derived result.

4) Presence/absence of a sleep disorder, such as insomnia and narcolepsy, may be diagnosed.

That is, since the determined sleep stage is used as basic data for diagnosing a sleep disorder, accurately determining the sleep stage may become a very important issue for diagnosis.

However, as described above, although even trained experts perform a sleep stage analysis in a manual manner, a great error may occur due to atypia of an irregular brain wave, which differs for each patient, and a complex scoring rule of the American Academy of Sleep Medicine (AASM) that is a determination standard.

In particular, in some cases, even experts may not have a matching opinion about an issue of classifying a sleep stage. Further, when a person reads a polysomnography result corresponding to an average of eight hours one by one, a human error may occur and may also affect the above error.

A research result of an existing document related thereto is disclosed in "Interrater reliability for sleep scoring according to the Rechtschaffen & Kales and the new AASM standard" of "Journal of Sleep Research 2009 18, 74 to 84" published in 2009. According to this paper, evaluation results from 7 experts show a matching degree of 82% based on an AASM standard and 80.6% based on a Rechtschaffen & Kales standard.

Accordingly, it is verified that an error of about 20% is present among the skilled experts with respect to a result of analyzing a sleep stage for an actual sleep related diagnosis.

Automation using software may reduce an error between humans and a reading time.

However, due to the aforementioned irregular brain waves and complex sleep stage determination rule, it may be significantly difficult to configure software that is configured to determine a sleep stage using an existing signal processing method, such as, for example, Korean Registration Patent No. 10-1395197 titled "method and apparatus for automatically detecting a sleep stage and a waking state".

SUMMARY

An aspect is to provide software that may analyze a sleep stage using a deep learning and read a result of analyzing the sleep stage more quickly and accurately than a person.

Also, an aspect is to provide an objective standard according to a sleep stage determination by determining a sleep stage using an artificial intelligence (AI).

Also, an aspect is to reduce a determination error between experts through an objective standard according to a sleep stage determination.

Also, an aspect is to provide a polysomnography apparatus that may minimize an amount of time used for performing polysomnography by automating a polysomnography result analysis through a sleep state determination model and a method of operating polysomnography.

Also, an aspect is to provide a polysomnography apparatus that may improve accuracy and reliability of polysomnography by generating a sleep stage determination model through a machine training based on an artificial neural network in which a convolution neural network (CNN) and a recurrent neural network (RNN) are combined and a method of operating the polysomnography apparatus.

According to an aspect of at least one example embodiment, there is provided a data processing apparatus including a signal data processor configured to collect signal data detected through polysomnography, to extract feature data by analyzing a feature of the collected signal data, and to transform the extracted feature data to time series data; and a sleep stage classification model processor configured to input the processed signal data to a pre-generated sleep stage classification model, and to classify a sleep stage corresponding to the signal data.

The signal data may be collected in a European data format (EDF) from a plurality of different equipments, and the signal data processor may include a data selector configured to unify a key value that approaches the signal data, a sampling frequency value, a type of the signal data, and a format of the signal data.

The data selector may be configured to manage the signal data using a unified key value by defining a virtual key for each piece of the signal data and by mapping different key values of the same signal data to the defined virtual keys.

The data selector may be configured to manage the signal data using a unified sampling frequency by defining a different sampling frequency for each piece of the collected signal data as a value of two or more folds of a Nyquist frequency through at least one of up-sampling and down-sampling.

The data selector may be configured to collect the signal data using predefined channels, and to unify a number of signal channels for each polysomnography equipment and inspection type through channel addition or addition duplication for the predefined channel.

The data selector may be configured to, when an omission of the signal data occurs in a channel for collecting the EEG signal or a channel for collecting the EOG signal or when the signal data is excluded from the polysomnography, replace the EEG signal with another EEG signal present at a most adjacent position among the same ground signals, and to replace the EOG signal with a signal present at a position opposite to a position of an omitted signal.

The signal data may be collected in an EDF from a plurality of different equipments, and the signal data processor may include a data correction processor configured to process a correction or an interpolation of the signal data for an omitted portion in response to an omission of the portion of the signal data.

The data correction processor may be configured to measure a secondary change rate of the signal data, to blank-process a portion in which the measured secondary change rate is largest in the signal data, and to restore a signal of a defect portion by performing a primary interpolation on the blank-processed portion.

The signal data processor may further include a data feature analyzer configured to extract feature data by analyzing a feature of each of an electroencephalographic (EEG) signal, an electro-oculographic (EOG) signal, and an electromyographic (EMG) signal with respect to the signal data, and to transform the extracted feature data to an epoch unit of time series data to input the extracted feature data to the pre-generated sleep stage classification model.

The sleep stage classification model processor may be configured to classify the sleep stage based on at least one of an American Academy of Sleep Medicine (AASM) standard and a Rechtschaffen and Kales (R&K) standard using an epoch unit of time series data as the processed signal data.

The data processing apparatus may further include a sleep stage classification model generator configured to generate the sleep stage classification model. The sleep stage classification model generator may include an inference modeler configured to define statistical sequence data of each sleep stage for inferring the sleep stage classification model by sequentially applying an input layer, a one-dimensional (1D) convolution layer, a long short-term memory (LSTM) layer, and a softmax layer.

The input layer may transform the signal data processed in a form of the time series data to a preset data size and forward the transformed signal data to the 1D convolution layer, the 1D convolution layer may learn a feature value required for sleep stage classification in an input tensor and forward the learned feature value to the LSTM layer, and the LSTM layer may learn the learned feature value based on a pattern according to a time and output an expectation value based on a finally learned pattern, and the softmax layer may output the expectation value as a statistical value and generate statistical sequence data of each sleep stage, thereby defining a final output.

The sleep stage classification model generator may further include an inference model trainer configured to train the inferred sleep stage classification model. The inference model trainer may be configured to perform a training by processing all of the sets of the detected signal data through a processor, by caching the processed signal data for each set in a storage device, and by loading the cached signal data for each set. Here, the inference model trainer may 1) load data based on a single set, 2) output the loaded data and perform a training using output data, 3) measure and store a training result, 4) apply a process of 1) to 3) with respect to the entire data and terminate a training 1 epoch when the progress is completed with respect to the entire sets, and 5) repeat a process of 4) by a predefined training epoch.

The sleep stage classification model generator may further include an inference model validator configured to compare a test set acquired from a distribution of collected samples and a result of the inferred sleep stage classification model.

The data processing apparatus may further include an inference model performance improver. The inference model performance improver may include a service module configured to output a sleep stage classification result for the processed signal data by deploying a sleep stage classification model having a currently validated highest performance, a training module configured to iteratively conduct a search on a hyperparameter of the deployed sleep stage classification model and to validate the deployed sleep stage classification model based on the iterative search result, and a database configured to store validation data acquired by validating the sleep stage classification model. The training module may compare the stored validation data and the performance of the sleep stage classification model being currently deployed and serviced and may control the service module to deploy the sleep stage classification model having a relatively excellent performance.

According to an aspect of at least one example embodiment, there is provided an operation method of a data processing apparatus, the method including collecting signal data detected through polysomnography; extracting feature data by analyzing a feature of each of an EEG signal, an EOG signal, and an EMG signal with respect to the collected signal data; transforming the extracted feature data to an epoch unit of time series data to input the extracted feature data to a pre-generated sleep stage classification model; and inputting the processed signal data to the pre-generated sleep stage classification model and classifying a sleep stage corresponding to the signal data.

When an omission of the signal data occurs in a channel for collecting the EEG signal or a channel for collecting the EOG signal or when the signal data is excluded from the polysomnography, the collecting of the signal data may include replacing the EEG signal with another EEG signal present at a most adjacent position among the same ground signals and replacing the EOG signal with a signal present at a position opposite to a position of an omitted signal.

The collecting of the signal data may include processing a correction or an interpolation of the signal data for an omitted portion in response to an omission of the portion of the signal data, and the processing the correction or the interpolation may include measuring a secondary change rate of the signal data; blank-processing a portion in which the measured secondary rate is largest; and restoring a signal of a defect portion by performing a primary interpolation on the blank-processed portion.

The operation method of the data processing apparatus may further include generating the sleep stage classification model. The generating of the sleep stage classification model may include defining statistical sequence data of each sleep stage for inferring the sleep stage classification model by sequentially applying an input layer, a 1D convolution layer, an LSTM layer, and a softmax layer. The defining of the statistical sequence data may include transforming the signal data processed in a form of the time series data to a preset data size and forwarding the transformed signal data to the 1D convolution layer; learning a feature value required for sleep stage classification in an input tensor and forwarding the learned feature value to the LSTM layer; learning the learned feature value based on a pattern according to a time and outputting an expectation value based on a finally learned pattern; and outputting the expectation value as a statistical value and generating statistical sequence data of each sleep stage, thereby defining a final output.

The operation method of the data processing apparatus may further include improving an inference model performance. The improving of the inference model performance may include outputting a sleep stage classification result for the processed signal data by deploying a sleep stage classification model having a currently validated highest performance; iteratively conducting a search on a hyperparameter of the deployed sleep stage classification model; validating the deployed sleep stage classification model based on the iterative search result; storing validation data acquired by validating the sleep stage classification model; and comparing the stored validation data and the performance of the sleep stage classification model being currently deployed and serviced and controlling the service module to deploy the sleep stage classification model having a relatively excellent performance.

According to some example embodiments, it is possible to provide software that may analyze a sleep stage using a deep learning and read a result of analyzing the sleep stage more quickly and accurately than a person.

Also, according to some example embodiments, it is possible to provide an objective standard according to a sleep stage determination by determining a sleep stage using an artificial intelligence (AI).

Also, according to some example embodiments, it is possible to reduce a determination error between experts through an objective standard according to a sleep stage determination.

Also, according to some example embodiments, it is possible to minimize an amount of time used for performing polysomnography by automating a polysomnography result analysis through a sleep state determination model.

Also, according to some example embodiments, it is possible to improve accuracy and reliability of polysomnography by generating a sleep stage determination model through a machine training based on an artificial neural network in which a convolution neural network (CNN) and a recurrent neural network (RNN) are combined.

Further areas of applicability will become apparent from the description provided herein. The description and specific examples in this summary are intended for purposes of illustration only and are not intended to limit the scope of the present disclosure.

BRIEF DESCRIPTION OF THE FIGURES

Example embodiments will be described in more detail with regard to the figures, wherein like reference numerals refer to like parts throughout the various figures unless otherwise specified, and wherein.

DETAILED DESCRIPTION

Figure 1:
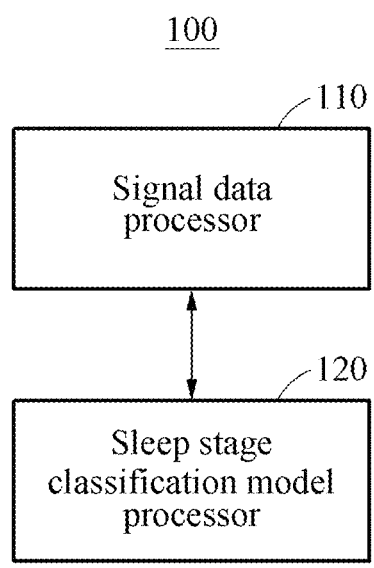
FIG. 1 is a diagram illustrating an example of a data processing apparatus according to an example embodiment.

The following structural or functional descriptions of example embodiments described herein are merely intended for the purpose of describing the example embodiments described herein and may be implemented in various forms. Here, the examples are not construed as limited to the disclosure and should be understood to include all changes, equivalents, and replacements within the idea and the technical scope of the disclosure.

Various modifications and changes may be made to the present disclosure and the disclosure may include various example embodiments. Specific example embodiments are described in detail with reference to the accompanying drawings. The example embodiments, however, may be embodied in various different forms, and should not be construed as being limited to only the specific example embodiments. Rather, the example embodiments should be understood to include all of the modifications, equivalents, and substitutions included in the spirit and technical scope of the disclosure.

Although the terms "first", "second", etc., may be used herein to describe various components, the components should not be limited by these terms. These terms are only used to distinguish one component from another component. For example, a first component may also be termed a second component and, likewise, a second component may be termed a first component, without departing from the scope of this disclosure.

When a component is referred to as being "connected to" or "coupled to" another component, the component may be directly connected to or coupled to the other component, or one or more other intervening components may be present. In contrast, when a component is referred to as being "directly connected to" or "directly coupled to", there is no intervening component. Further, expressions describing a relationship between components, such as "~between" and "directly between~" or "directly neighboring to" should be understood likewise.

The terms used herein are used to simply explain specific example embodiments and are not construed to limit the present disclosure. The singular forms "a", "an", and "the", are intended to include the plural forms as well, unless the context clearly indicates otherwise. It will be further understood that the terms "comprises/comprising," and "has/having" when used in this specification, specify the presence of stated features, integers, steps, operations, elements, and/or components, but do not preclude the presence or addition of one or more other features, integers, steps, operations, elements, components, and/or groups, thereof.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Hereinafter, example embodiments will be described in detail with reference to the accompanying drawings. For simplicity of description and general understanding of the disclosure, like reference numerals refer to like components throughout the present specification although they are illustrated in different drawings.

FIG. 1 is a diagram illustrating an example of a data processing apparatus 100 according to an example embodiment.

The data processing apparatus 100 may determine a sleep stage using artificial intelligence (AI) and may provide an objective standard according to a sleep stage determination. Through this, a determination error between experts may decrease and an amount of time used for performing polysomnography may be minimized by automating a polysomnography result analysis.

Referring to FIG. 1, the data processing apparatus 100 may include a signal data processor 110 and a sleep stage classification model processor 120.

The signal data processor 110 may provide an input to an AI model. In particular, the signal data processor 110 may provide a polysomnography result as an input to the AI model.

In detail, the signal data processor 110 may collect signal data detected through polysomnography for the input to the AI model and may extract feature data by analyzing a feature of the collected signal data. Also, the signal data processor 110 may transform the extracted feature data to time series data and may provide the input to the AI model.

The signal data detected through the polysomnography may be interpreted as biometric data that is measured from a subject through at least one detection device among an electroencephalogram (EEG) sensor, an electrooculography (EOG) sensor, an electromyogram (EMG) sensor, an electrokardiogramme (EKG) sensor, a photoplethysmography (PPG) sensor, a chest belt, an abdomen belt, a thermistor, a flow sensor, and a microphone.

For example, the signal data detected through the polysomnography may be interpreted as data that is collected in real time and may also be interpreted as data that is recorded in a polysomnography database through previously performed polysomnography.

Also, the sleep stage classification model processor 120 may input the processed signal data to a pre-generated sleep stage classification model and may classify a sleep stage corresponding to the signal data.

The pre-generated sleep stage classification model may classify the sleep stage based on at least one of an American Academy of Sleep Medicine (AASM) standard and a Rechtschaffen and Kales (R&K) standard using an epoch unit of time series data as the AI model, as represented by the following Table 1.

TABLE 1

| AASM | Wake | Rem | N1 stage | N2 stage | N3 stage | |
|---|---|---|---|---|---|---|
| R&K | Wake | Rem | N1 stage | N2 stage | N3 stage | N4 stage |

The sleep stage classification model processor 120 may classify the sleep stage by applying an AASM sleep stage scoring rule or an R&K sleep stage scoring rule to the processed signal data.

Hereinafter, an example embodiment in which the sleep stage classification model processor 120 classifies the sleep stage using, for example, the AASM sleep stage scoring rule is described.

The signal data processor 110 may collect and process the entire sleep data that is measured based on a unit, for example, epoch, of 30 seconds.

The sleep stage classification model processor 120 may classify the sleep stage into a "Wake" stage if at least one feature among alpha rhythm, eye blinks (0.5~2 Hz), a rapid eye movement associated with normal or high chin muscle tone, and a reading eye movement is 50% or more.

Also, the sleep stage classification model processor 120 may classify the sleep stage into a "Rem" stage if a low amplitude without K-complex and sleep spindle, a mixed-frequency EEG activity, and a rapid eye movement in a low chin EMG tone epoch simultaneously appear.

Also, the sleep stage classification model processor 120 may classify the sleep stage into the "Rem" stage if an arousal occurs, or before a signal of a "W" stage or an "N3" stage, and a body movement occurs.

Also, the sleep stage classification model processor 120 may classify the sleep stage into an "N1" stage if the alpha rhythm is weak or if the low amplitude and the mixed-frequency activity are 50% or more of an epoch as a result of analyzing the processed signal data.

Also, the sleep stage classification model processor 120 may classify the sleep stage into the "N1" stage for at least one of cases including an occurrence of theta (4~7 Hz) rhythm, an occurrence of slow eye movements (SEM), an occurrence of arousal in an "N2" stage, and an occurrence of arousal in the "Rem" stage.

The sleep stage classification model processor 120 may classify the sleep stage into the "NT" stage at a time at which or after K-complex and sleep spindle occur, if the low amplitude and the mixed-frequency activity are 50% or more of an epoch with K-complex and sleep spindle, and if an N3 feature does not appear in an "N3" stage as a result of analyzing the processed signal data.

Also, the sleep stage classification model processor 120 may classify the sleep stage into the "N3" stage if 20% of the epoch is less than or equal to a slow wave activity of 0.5~2 Hz and a peak to peak amplitude of 75microV as a result of analyzing the processed signal data.

In the "N3" stage, the K complex may be regarded as the slow wave activity and the sleep spindle may coexist in the N3 stage. Also, an eye movement may barely occur and EMG may be maintained at a relatively low amplitude compared to that in the "N2" stage.

The N3 stage of the AASM sleep stage scoring rule may replace the N3 stage and the stage N4 stage of the R&K sleep stage scoring rule.

The following Table 2 shows a pattern of signal data validated for each sleep stage.

TABLE 2

| | | Stage | | | | |
|---|---|---|---|---|---|---|
| Signal | Pattern | Wake | Stage N1 | Stage N2 | Stage N3 | Stage Rem |
| EEG | Slow delta | No | No | No | Yes | No |
| | Theta | DK | Yes | DK | DK | Yes |
| | Sleep spindle | No | No | Yes | DK | No |
| EOG | REM signal | Yes | No | No | No | Yes |
| EMG | Muscle Tone | Yes | DK | DK | DK | No |

※ DK: Don't Care

The sleep stage classification model processor 120 according to example embodiments may generate a sleep state determination model through machine training based on an artificial neural network in which a convolution neural network (CNN) and a recurrent neural network (RNN) are combined, thereby improving accuracy and reliability of the scoring results of polysomnography.

Figure 2:
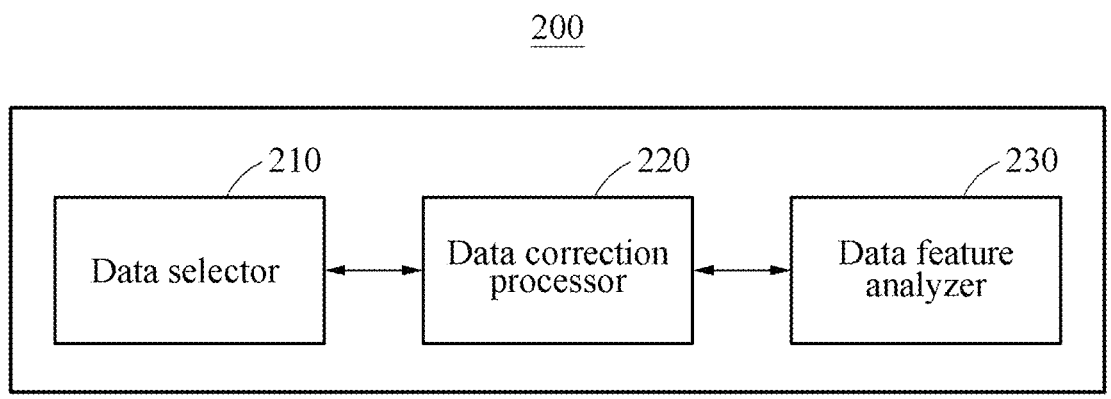
FIG. 2 is a diagram illustrating an example of a signal data processor according to an example embodiment.

FIG. 2 is a diagram illustrating an example of a signal data processor 200 according to an example embodiment.

The signal data processor 200 may perform processing to input signal data to an AI model.

For example, the signal data may be collected in a European data format (EDF) from a plurality of different equipments. For reference, signal data used by equipments employed for the polysomnography may be distributed and managed in an EDF file format.

The plurality of equipments may include equipment using at least one sensor among an EEG sensor required for polysomnography, an EOG sensor, an EMG sensor, an EKG sensor, a photoplethysmography (PPG) sensor, a chest belt, an abdomen belt, a thermistor, a flow sensor, and a microphone, which are required for polysomnography.

To perform processing, the signal data processor 200 may include a data selector 210, a data correction processor 220, and a data feature analyzer 230.

A key value that approaches the signal data in an EDF file, a sampling frequency value, a type of a signal, and a number of signals may differ for each piece of polysomnography equipment, for each hospital, and for each inspection. The data selector 210 included in the signal data processor 200 may be a module configured to unify the key value, the sampling frequency value, and a format of the type of the signal.

That is, the data selector 210 may perform processing of unifying formats of signal data input from various equipments.

For example, the data selector 210 may unify a key value that approaches signal data, a sampling frequency value, a type of the signal data, and a format of the signal data. In particular, the data selector 210 may manage the signal data using a unified key value by defining a virtual key for each piece of the signal data and by mapping different key values of the same signal data to the defined virtual keys.

The data selector 210 may manage the signal data using a unified sampling frequency by defining a different sampling frequency for each piece of the collected signal data as a value of two or more folds of a Nyquist frequency through at least one of up-sampling and down-sampling.

Also, the data selector 210 may collect signal data using predefined channels and may unify a number of signal channels for each polysomnography equipment and inspection type through channel addition or channel duplication for the predefined channels.

Accordingly, the data selector 210 may perform a determination using a minimum number of signals by unifying a number of signal channels for each polysomnography equipment and for each inspection type. Also, a deep learning polysomnography apparatus may support various EEG signals, such as 2 channel (2CH), 4CH, and 6CH, by unifying a number of signal channels for each polysomnography equipment and each inspection type.

While collecting signal data, an omission or a deformation of data may occur, which may lead to affecting a result of determining a sleep stage.

To complement the above situation, the data selector 210 may performing processing of the signal data.

For example, the data selector 210 may verify a case in which an omission of signal data occurs in a channel for collecting an EEG signal or a channel for collecting an EOG signal or a case in which the signal data is excluded from polysomnography.

In response thereto, the data selector 210 may replace the EEG signal with another EEG signal present at a most adjacent position among the same ground signals. The EEG signal is replaceable due to a feature that adjacent EEG signals are collected in a similar form. Also, the data selector 210 may replace the EOG signal with a signal present at a position opposite to a position of an omitted signal. Likewise, the EOG signal is replaceable due to a feature that a pair of signals collected at opposite sides are in a similar form.

For example, although the input signal data is defined as EEG 6CH, EOG 2CH, and EMG 1CH, a number of signal channels differs for each polysomnography equipment and for each inspection type. Therefore, a format may be unified by adding and duplicating a channel.

If a signal omission occurs with respect to EEG 6CH and EOG 2CH signals or if a corresponding signal is excluded from polysomnography, the EEG signal may be replaced with a signal present at a most adjacent position among the same ground signals and the EOG signal may be replaced with a signal present at a position opposite to a position of the omitted signal.

TABLE 3

| | Virtual Key | LAB1 Key | LAB1 Hz | LAB2 Key | LAB2 Hz |
|---|---|---|---|---|---|
| EEG | F4-M1 | F4-M1 | 500 –> TSF | EEG | 125 –> TSF |
| | F3-M2 | F3-M2 | 500 –> TSF | EEG2 | 125 –> TSF |
| | C4-M1 | C4-M1 | 500 –> TSF | EEG | 125 –> TSF |
| | C3-M2 | C3-M2 | 500 –> TSF | EEG2 | 125 –> TSF |
| | O2-M1 | O2-M1 | 500 –> TSF | EEG | 125 –> TSF |
| | O1-M2 | O1-M2 | 500 –> TSF | EEG2 | 125 –> TSF |

TABLE 3-continued

|  | Virtual Key | LAB1 Key | LAB1 Hz | LAB2 Key | LAB2 Hz |
|---|---|---|---|---|---|
| EOG | LOC | LOC | 500 –> TSF | EOG(L) | 125 –> TSF |
|  | ROC | ROC | 500 –> TSF | EOG(R), ROC-0 | 125 –> TSF |
| EMG | EMG | Chin | 500 –> TSF | EMG | 125 –> TSF |

In Table 3, TSF represents a specific target sampling frequency.

Table 3 shows a difference in each of a key, a sampling frequency, and a number of signal and a method of unifying the difference for each LAB.

In response to an omission of a portion of collected signal data, the data correction processor 220 may process a correction or an interpolation of the signal data for the omitted portion.

In detail, the data correction processor 220 may measure a differential value as a secondary change rate for the signal data, may blank-process a portion in which the measured secondary change rate is largest in the signal data, and may restore a signal of a defect portion by performing a primary interpolation on the blank-processed portion.

The data feature analyzer 230 may extract feature data by analyzing a feature of each of an EEG signal, an EOG signal, and an EMG signal with respect to the signal data, and may transform the extracted feature data to an epoch unit of time series data to input the extracted feature data to a pre-generated sleep stage classification model.

In detail, if the signal data includes an EEG signal, the data feature analyzer 230 may perform an EEG feature analysis.

The data feature analyzer 230 may calculate a line length in a time domain to analyze a feature of the EEG signal with respect to the signal data.

A numerical number of the line length may be used to measure an amplitude and a frequency vibration of the EEG signal in the signal data. The line length may be calculated according to the following Equation 1.

$$\text{Line Length} = \sum_{n=2}^{N} |x_n - x_{n-1}|,\quad \text{[Equation 1]}$$

Also, the data feature analyzer 230 may calculate Kurtosis to measure a presence and a position of an extreme value within an EEG signal epoch according to the following Equation 2.

$$\text{Kurtosis} = E\left[\left(\frac{X-\mu}{\sigma}\right)^4\right]\quad \text{[Equation 2]}$$

The data feature analyzer 230 may use a feature defined in a frequency domain.

The data feature analyzer 230 may generate a spectrogram using a fast Fourier transform (FFT) or a MTSA (multi-taper spectral analysis) to analyze a frequency of the EEG signal.

Also, the data feature analyzer 230 may set a size of a window by setting time domain data of a 30-second epoch as a unit time and may perform MTSA by sliding the window at intervals less than the unit time.

The data feature analyzer 230 may obtain a power ratio of a frequency bin with respect to F, O, and C data of the EEG signal based on a definition of a frequency domain feature by binning a frequency band according to the following Table 4 and may use 95 percentile, a minimum, mean, and standard deviation of spectrogram as feature data for the AI model.

TABLE 4

| Delta wave | 0~0.399 Hz |
|---|---|
| Theta wave | 4~7.99 Hz |
| Alpha wave | 8~13 Hz |
| Beta wave | 13 Hz or more |

Therefore, {F, C, O} *{95 Percentile, minimum, mean, standard deviation}=12 Features.

Further, the data feature analyzer 230 may use Kurtosis of the spectrogram as feature data for transient bursts such as sleep spindle.

Also, if the signal data includes an EOG signal, the data feature analyzer 230 may perform an EOG feature analysis.

The data feature analyzer 230 may apply an energy constant band (ECB) of a power spectrum in which two EOG signals are defined as two pieces of feature data.

The energy constant band (ECB) of the power spectrum P(f) may be calculated according to the following Equation 3.

$$ECB = \int_{fl=0.35\ Hz}^{fh=0.5\ Hz} P(f)\quad \text{[Equation 3]}$$

If the signal data includes an EMG signal, the data feature analyzer 230 may perform an EMG feature analysis.

To this end, the data feature analyzer 230 may use an energy signal that defines the EMG signal as a single piece of feature data.

Figure 3:
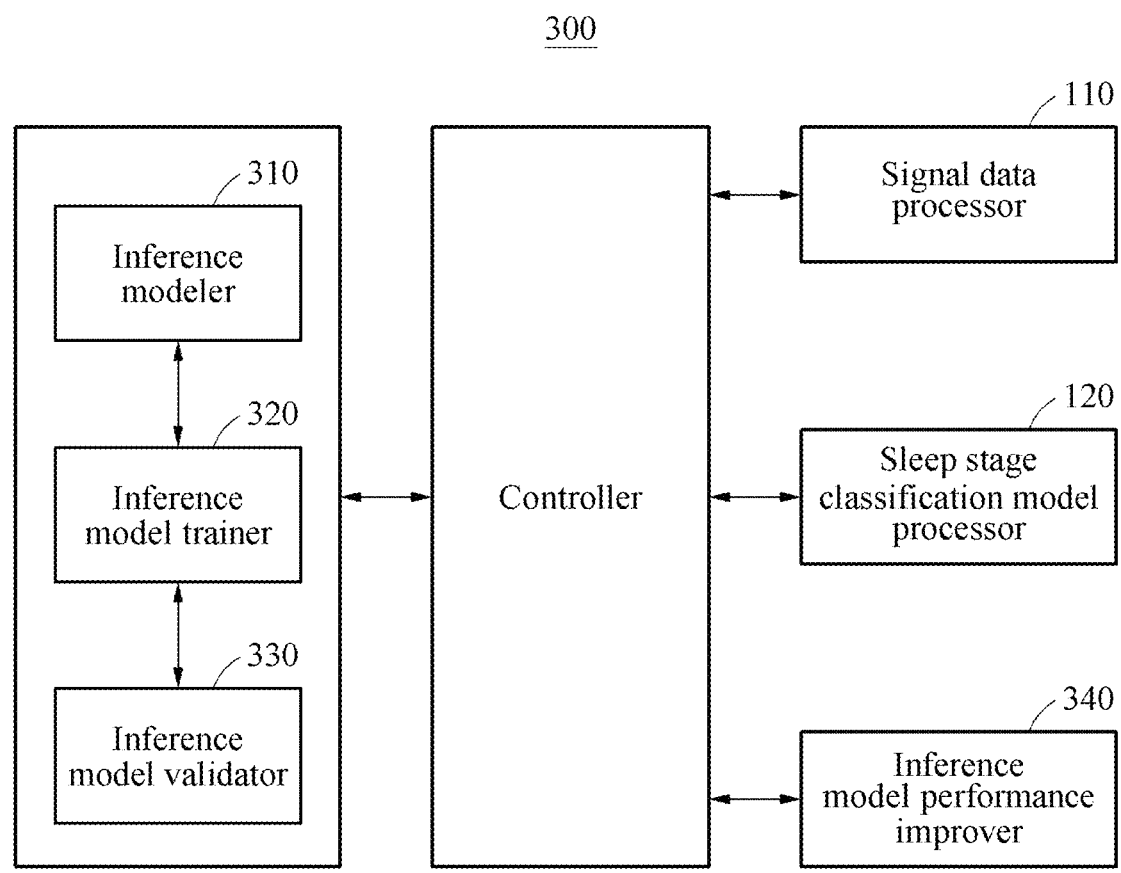
FIG. 3 is a diagram illustrating another example of a data processing apparatus according to an example embodiment.

FIG. 3 illustrates an example of a data processing apparatus 300 according to an example embodiment.

The data processing apparatus 300 may include a sleep stage classification model generator configured to generate a sleep stage classification model.

The AI-based sleep stage classification model may classify a sleep stage by receiving an epoch unit of time series data having a processed feature and by analyzing a signal pattern using a deep learning technique.

To achieve the sleep stage classification model with an optimal performance, a hyperparameter is present and is defined for each layer.

The sleep stage classification model according to an example embodiment may be designed in a form of a deep learning model based on a CNN and an RNN.

Referring to FIG. 3, the sleep stage classification model generator may include an inference modeler 310, an inference model trainer 320, and an inference model validator 330.

The inference modeler 310 may define statistical sequence data of each sleep stage for inferring the sleep stage classification model by sequentially applying an input layer, a one-dimensional (1D) convolution layer, a long short-term memory (LSTM) layer, and a softmax layer.

Figure 4:
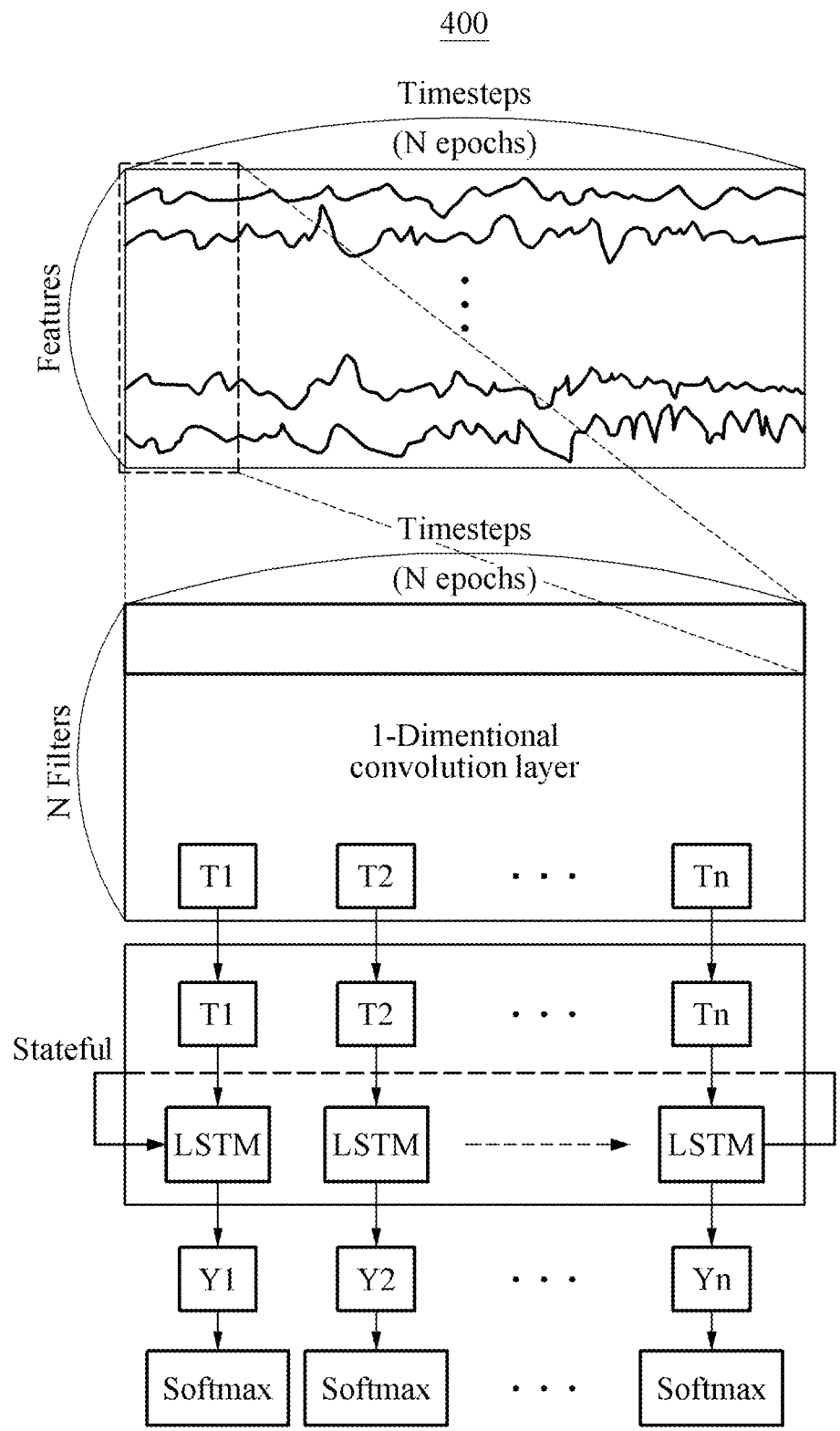
FIG. 4 illustrates an example of components of an artificial intelligence (AI) model according to an example embodiment.

A structure of a sleep stage classification model 400 of FIG. 4 may be used to describe the components of FIG. 3. The sleep stage classification model may correspond to an AI model.

Initially, the input layer may transform signal data processed in a form of time series data to a preset data size and forward the transformed signal data to the 1D convolution layer.

The 1D convolution layer may learn a feature value required for sleep stage classification in an input tensor and forward the learned feature value to the LSTM layer.

Also, the LSTM layer may learn the learned feature value based on a pattern according to a time and output an expectation value based on a finally learned pattern, and the softmax layer may output the expectation value as a statistical value and generate statistical sequence data of each sleep stage, thereby defining a final output.

The inference model trainer 320 may perform a training by processing all of the sets of the detected signal data through a processor, by caching the processed signal data for each set in a storage device, and by loading the cached signal data for each set. During a training process, the inference model trainer 320 may 1) load data based on a single set, 2) output the loaded data and perform a training using output data, 3) measure and store a training result, and 4) apply a process of 1) to 3) with respect to the entire data. Once the progress is completed using a process of 1) to 4) as a single epoch, training 1 epoch may be terminated. Also, the inference model trainer 320 may repeat a process of 4) by a predefined training epoch.

The inference model validator 330 may compare a test set acquired from a distribution of collected samples and a result of the inferred sleep stage classification model.

The data processing apparatus 300 may further include an inference model performance improver 340.

The inference model performance improver 340 may include a service module, a training module, and a database.

The inference model performance improver 340 may output a sleep stage classification result for the processed signal data by deploying a sleep stage classification model having a currently validated highest performance through the service module.

Also, the training module may iteratively conduct a search on a hyperparameter of the deployed sleep stage classification model and may validate the deployed sleep stage classification model based on the iterative search result.

The database may store validation data acquired by validating the sleep stage classification model.

The training module may compare the stored validation data and the performance of the sleep stage classification model being currently deployed and serviced and may control the service module to deploy the sleep stage classification model having a relatively excellent performance.

A sleep stage analysis using only a CNN may be used to construct an AI network by using 30 seconds as a single epoch. In this case, a sleep stage may be classified by constructing the CNN into consideration of EEG, EOG and chin-EMG signals as a single image.

An RNN may be an AI model suitable for constructing a signal using EEG, EOG and chin-EMG signals.

In the case of using actual EEG, EOG, and chin-EMG raw data using only the RNN, data of 30 seconds and data before and after 30 seconds need to be processed. Therefore, in the case of using the RNN, it is possible to reduce a number of stages required for the RNN and to reduce an operation time used up to output using an actual AI by analyzing the EEG, EOG, and chin-EMG raw data based on a unit of 30 seconds and by defining and using features according thereto as an input.

The sleep stage classification model according to an example embodiment may use a combination of the CNN and the RNN.

A model may be constructed by extracting features from time variant signals, such as an audio signal and a biosignal. Alternatively, a multi-layer CNN may be constructed to extract features from raw data. The extracted features may be combined with the RNN.

A representative example thereof may be SoundNet. However, due to a complexity in a number of layers included in the CNN, a large amount of time and calculation may be used in terms of a training efficiency.

In contrast, the sleep stage classification model according to an example embodiment may define features of biosignals and provide the defined features every 30 seconds, thereby reducing an amount of calculation and training time used by a deep learning model.

FIG. 4 illustrates an example of an AI model 400 according to an example embodiment.

As described above, the sleep stage classification model may follow a form of the AI model 400.

The AI model 400 may be represented using four layers, for example, an input layer, a 1D convolution layer, an LSTM layer, and a softmax layer.

In detail, the input layer may serve to transform time series data processed through a processor to a data size and may forward the transformed data to a subsequent layer.

A shape of input data is referred to as a tensor shape. The tensor shape may vary based on a degree of optimization of a classification model, which may represent a batch size, timesteps, and features.

The batch size may vary based on a memory size of a graphics processor unit (GPU) that executes a prediction work of the classification model and may be interpreted as a hyperparameter of a timestep input layer.

A sleep stage classification of polysomnography is performed based on an epoch unit of 30 seconds. Therefore, time series data of the epoch unit may be input and a timestep value may represent a 30-second epoch. That is, if timestep value=50, it may represent data of 50 epochs.

The convolution layer may learn an optimal feature value required for sleep stage classification in an input tensor and may forward the learned feature value to a subsequent layer.

The hyperparameter of the convolution layer may include, for example, a number of filters, a size of a filter, a stride, and a padding.

A form of an output of the convolution layer may differ from a form of input data and may be represented as the following Equation 4.

$$\text{Output Timesteps} = \frac{\text{InputTimesteps} + 2\text{Padding} - \text{FilterSize}}{\text{Stride}} + 1 \quad \text{[Equation 4]}$$

A feature may need to be learned based on an epoch unit to classify a sleep stage based on the epoch unit. Here, a condition that input and output timesteps need to be identical is required.

To this end, a constraint condition on hyperparameters of the padding and the stride may be defined as the following Equation 5.

$$\text{Padding} = \frac{\text{FilterSize}}{2}, \text{Stride} = 1 \quad \text{[Equation 5]}$$

Here, a pooling layer generally used for the convolution layer is not used since the pooling layer is for down-sampling a time variant signal according to a Nyquist theory.

Down-sampling the time variant signal may cause an aliasing effect. In this case, an error may occur in training and classification of a sleep stage due to a signal distortion.

Accordingly, the pooling layer is not used herein for the sleep stage classification model.

The LSTM layer may learn the optimal feature value forwarded from the 1D convolution layer based on a pattern according to a time and may output an expectation value for the sleep stage based on a finally learned pattern.

The softmax layer may output the expectation value of the sleep stage output from the LSTM layer as a statistical value of 0 to 1, and may generate statistical sequence data of each sleep stage.

A unit of a data set for training the inferred model is a single set. The single set may include correct answer data and signal data acquired in such a manner that a single person performs polysomnography.

The data set may be stored in a form that variously varies ranging from 800 epochs to 1200 epochs for each single set.

A training and performance measurement unit may use a single set unit to measure an accuracy based on the single set unit instead of measuring the accuracy based on an epoch unit.

Since an existing framework does not efficiently support a training in the aforementioned manner, a separate training procedure based on a single set unit is designed and performed.

If a one-time backpropagation is performed on the entire data, a unit of training may be defined as a single epoch.

For reference, an epoch in training and an epoch that is a unit of time series data of polysomnography need to be distinguished.

As described above, there is a hyperparameter of which an optimal value needs to be found to generate the optimal performance of the inference model. Since such a hyperparameter range is wide, a search may be continuously conducted to find an optimal hyperparameter using a random search method and a Bayesian optimization method.

To protect the inference model trained through overfitting of the inferred model and a training interruption by a system error, a model weight may be stored based on an epoch unit and an unnecessary training may not be performed using an early stopping function. For example, the early stopping function refers to a function of forcefully stopping a training if a loss does not decrease by a predetermined epoch or more.

Figure 5:
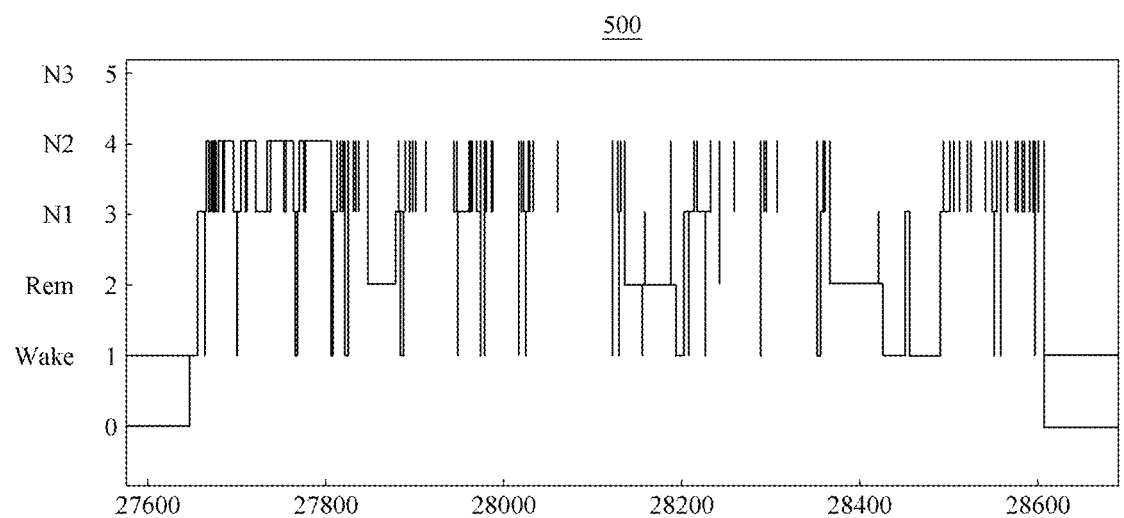
FIG. 5 is a graph showing an example of a matching degree of an output result from the AI model of FIG. 4.
Figure 6:
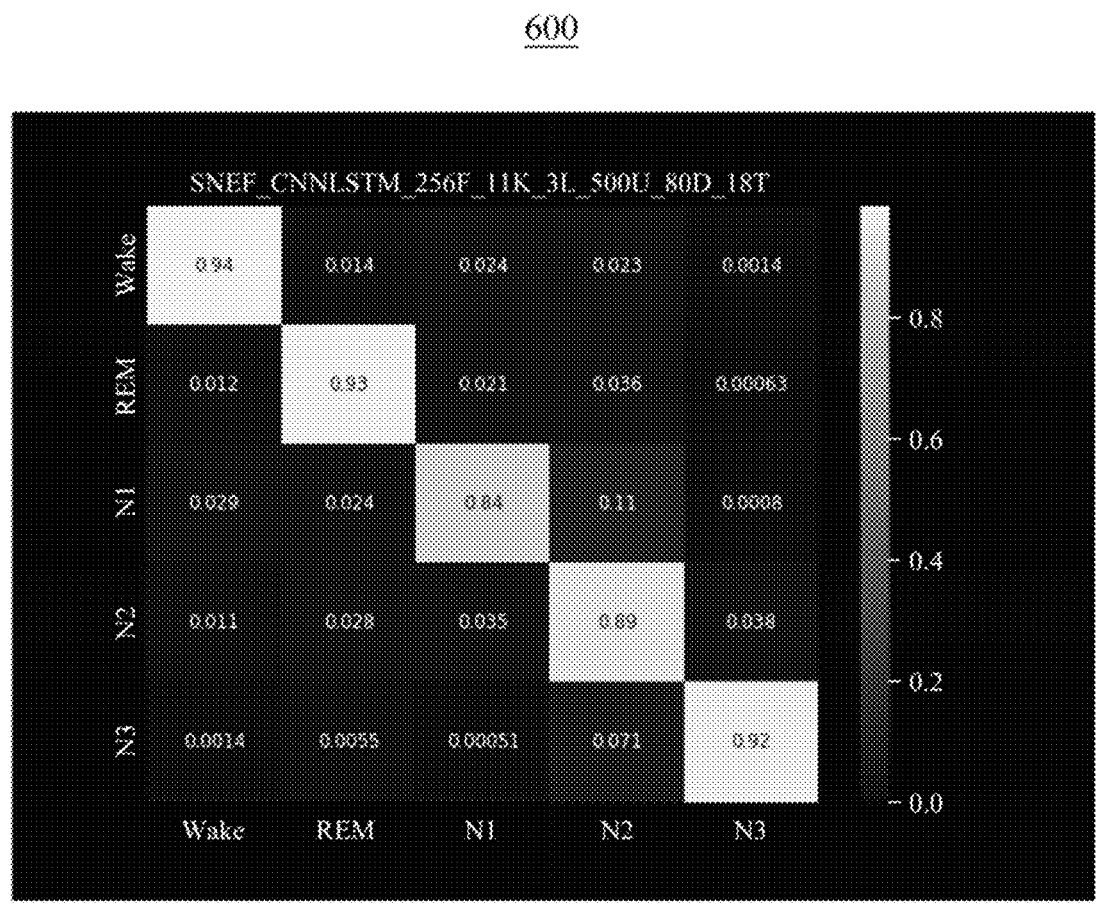
FIG. 6 illustrates an example of a matching degree of an output result from the AI model of FIG. 5.

FIG. 5 illustrates an example of a matching degree of an output result 500 from the AI model of FIG. 4, and FIG. 6 illustrates an example of a matching degree of an output result 600 based on existing data and the AI model.

Referring to the output result 500 of FIG. 5, a vertical axis represents each sleep stage and a horizontal axis represents a line length in a time domain.

Referring to the output result 600 of FIG. 6, although an objective index is present for each person performing a polysomnography scoring, a polysomnography data accuracy may slightly differ due to a subjective determination and may generally have a matching degree of about 0.75 Kappa.

Herein, to outperform the above issue, the accuracy may be improved by collecting samples with various distributions and by constructing a data set using the collected samples. Also, the accuracy of an algorithm may be secured by setting an accurate standard test set through agreement of various sleep articles.

Figure 7:
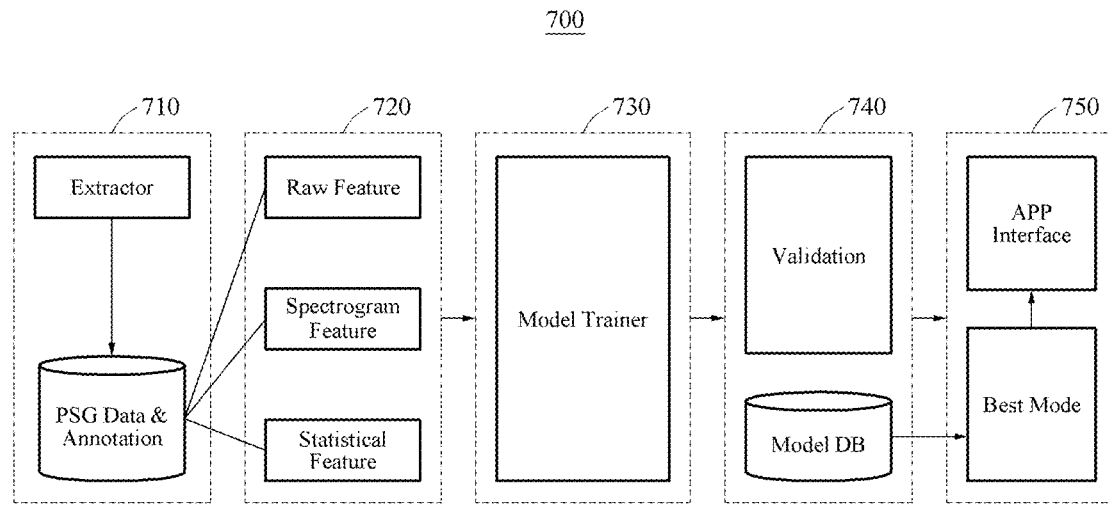
FIG. 7 is a diagram illustrating an example of components of a data processing apparatus according to an example embodiment.

FIG. 7 is a diagram illustrating an example of components of a data processing apparatus 700 according to an example embodiment.

Referring to FIG. 7, in operation 710, the data processing apparatus 700 may collect a polysomnography result.

In detail, in operation 710, the data processing apparatus 700 may extract the polysomnography result from a subject using an extractor or may collect the polysomnography result from a database that pre-stores the polysomnography result.

In operation 720, the data processing apparatus 700 may process the collected polysomnography result as signal data, and may process the collected polysomnography result using a raw data feature, a spectrogram feature, and a statistical feature through a processing process.

In operation 730, the data processing apparatus 700 may train a processed and inferred model using a model trainer.

In operation 740, the data processing apparatus 700 may complete a validation of the inferred and trained model and may store validation data acquired through validation in a model database. In operation 750, the data processing apparatus 700 may perform a comparison using prestored data and may replace the existing model with a model having a relatively excellent performance depending on a comparison result.

That is, the data processing apparatus 700 may compare the stored validation data and a performance of a sleep stage classification model being currently deployed and serviced and may control the service module to deploy the sleep stage classification model having a relatively excellent performance.

Figure 8:
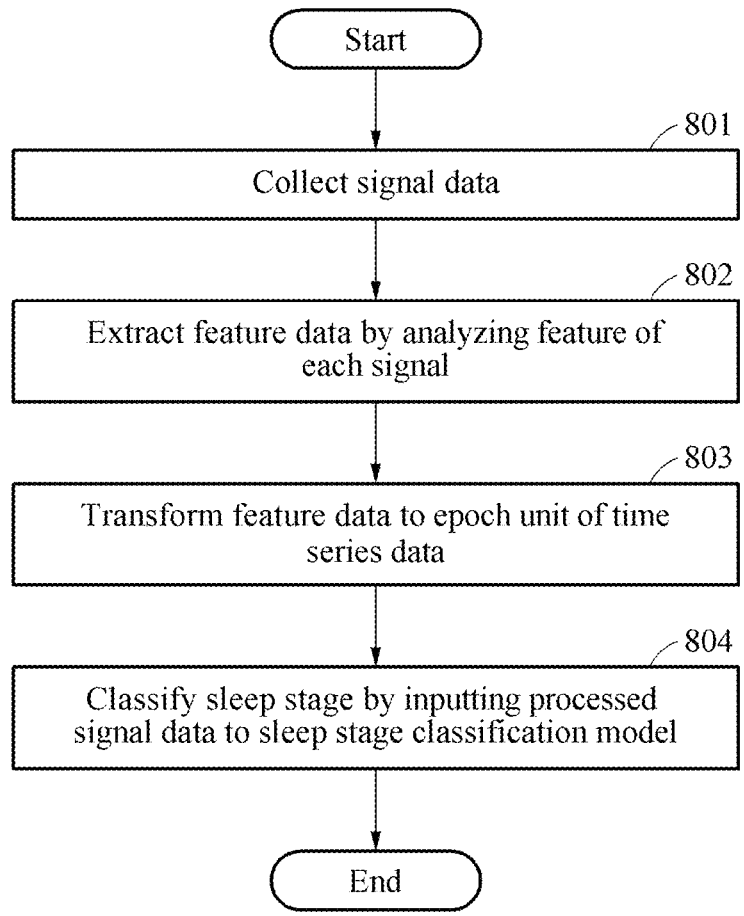
FIG. 8 is a flowchart illustrating an example of an operation method of a data processing apparatus according to an example embodiment.

FIG. 8 is a flowchart illustrating an example of an operation method of a data processing apparatus according to an example embodiment.

Referring to FIG. 8, in operation 801, the operation method of the data processing apparatus may collect signal data detected through polysomnography.

For example, a case in which an omission of signal data occurs in a channel for collecting an EEG signal or a channel for collecting an EOG signal or a case in which the signal data is excluded from polysomnography may be considered during a process of collecting the signal data. Here, the operation method of the data processing apparatus may replace the EEG signal with another EEG signal present at a most adjacent position among the same ground signals and may replace the EOG signal with a signal present at a position opposite to a position of an omitted signal.

Also, in response to an omission of a portion of the signal data during the process of collecting the signal data, the operation method of the data processing apparatus may perform a correction or an interpolation of the signal data for the omitted portion.

For example, to perform the correction or the interpolation of the signal data, the operation method of the data processing apparatus may measure a secondary change rate of the signal data, may blank-process a portion in which the measured secondary change rate is largest in the signal data, and may restore a signal of a defect portion by performing a primary interpolation on the blank-processed portion.

In operation 802, the operation method of the data processing apparatus may extract feature data by analyzing a feature of each of an EEG signal, an EOG signal, and an EMG signal with respect to the collected signal data.

The operation method of the data processing apparatus may transform the extracted feature data to an epoch unit of time series data in operation 803 to input the extracted feature data to a pre-generated sleep stage classification model, and may classify the sleep stage by inputting the processed signal data to the pre-generated sleep stage classification model in operation 804.

According to an example embodiment, the operation method of the data processing apparatus may further include an operation of generating the sleep stage classification model.

To this end, the operation method of the data processing apparatus may define statistical sequence data of each sleep stage by sequentially applying an input layer, a 1D convolution layer, an LSTM layer, and a softmax layer. The sleep stage may be inferred based on the defined statistical sequence data.

To define the statistical sequence data, the signal data processed in a form of time series data may be transformed to a predetermined data size and may be forwarded to the 1D convolution layer. Also, a feature value required for a sleep stage classification may be learned in an input tensor and the learned feature value may be forwarded to the LSTM layer.

The operation method of the data processing apparatus may learn the learned feature value as a pattern according to a time and may output an expectation value based on a finally learned pattern. In addition, the operation method of the data processing apparatus may generate statistical sequence data of each sleep stage by outputting the output expectation value as a statistical value, thereby defining a final output.

The operation method of the data processing apparatus may further include a process of improving a performance of an inference model.

To this end, the operation method of the data processing apparatus may output a sleep stage classification result for the processed signal data by deploying a sleep stage classification model having a currently validated highest performance. Also, the operation method of the data processing apparatus may iteratively conduct a search on a hyperparameter of the deployed sleep stage classification model and may validate the deployed sleep stage classification model based on the iterative search result. Also, the operation method of the data processing apparatus may store validation data acquired by validating the sleep stage classification model, and may compare the stored validation data and the performance of the sleep stage classification model being currently deployed and serviced and may control the service module to deploy the sleep stage classification model having a relatively excellent performance.

According to some example embodiments, it is possible to provide software that may analyze a sleep stage using a deep learning and read a result of analyzing the sleep stage more quickly and accurately than a person. Also, it is possible to provide an objective standard according to a sleep stage determination by determining a sleep stage using an AI.

Also, according to some example embodiments, it is possible to reduce a determination error between experts through an objective standard according to a sleep stage determination. Also, it is possible to minimize an amount of time used for performing polysomnography by automating a polysomnography result analysis through a sleep state determination model.

Also, according to some example embodiments, it is possible to improve accuracy and reliability of polysomnography by generating a sleep stage determination model through a machine training based on an artificial neural network in which a CNN and an RNN are combined.

The example embodiments described above may be implemented using hardware components, software components, and/or a combination thereof. For example, the apparatuses, the methods, and the components described herein may be implemented using one or more general-purpose or special purpose computers, such as, for example, a processor, a controller, an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and/or data may be embodied permanently or temporarily in any type of machine, component, physical equipment, virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more computer readable storage mediums.

The methods according to the above-described example embodiments may be recorded in non-transitory computer-readable media including program instructions to implement various operations of the above-described example embodiments. The media may also include, alone or in combination with the program instructions, data files, data structures, and the like. The media may continuously store a program executable by a computer or may temporarily store or the program for execution or download. Also, the media may be various types of recording devices or storage devices in which a single piece or a plurality of pieces of hardware may be distributed over a network without being limited to a medium directly connected to a computer system. Examples of the media include magnetic media such as hard disks, floppy disks, and magnetic tapes; optical media such as CD-ROM discs and DVDs; magneto-optical media such as floptical disks; and hardware devices that are specially configured to store and perform program instructions, such as read-only memory (ROM), random access memory (RAM), flash memory, and the like. Examples of other media may include recording media and storage media managed at Appstore that distributes applications or sites and servers that supply and distribute various types of software. Examples of program instructions include both machine code, such as produced by a compiler, and files containing higher level code that may be executed by the computer using an interpreter. The hardware devices may be configured to operate as at least one software module to perform operations of example embodiments, or vice versa.

While this disclosure includes specific example embodiments, it will be apparent to one of ordinary skill in the art that various alterations and modifications in form and details may be made in these example embodiments without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A data processing apparatus comprising:
a signal data processor configured to collect signal data detected through polysomnography, to extract feature data by analyzing a feature of the collected signal data, and to transform the extracted feature data to time series data; and
a sleep stage classification model processor configured to input the processed signal data to a pre-generated sleep stage classification model, and to classify a sleep stage corresponding to the signal data,
wherein the signal data processor is configured to extract feature data by analyzing a feature of each of an electroencephalographic (EEG) signal, an electro-oculographic (EOG) signal, and an electromyographic (EMG) signal with respect to the signal data, and to transform the extracted feature data to an epoch unit of time series data to input the extracted feature data to the pre-generated sleep stage classification model,
wherein the data processing apparatus includes a sleep stage classification model generator configured to generate the sleep stage classification model,
wherein the sleep stage classification model generator comprises:
an inference modeler configured to define statistical sequence data of each sleep stage for inferring the sleep stage classification model by sequentially applying an input layer, a one-dimensional (1D) convolution layer, a long short-term memory (LSTM) layer, and a softmax layer;
an inference model trainer configured to perform a training by processing all of the sets of the detected signal data through a processor, by caching the processed signal data for each set in a storage device, and by loading the cached signal data for each set; and
an inference model validator configured to compare a test set acquired from a distribution of collected samples and a result of the inferred sleep stage classification model,
wherein the data processing apparatus further comprises an inference model performance improver,
wherein the inference model performance improver comprises:
a service module configured to output a sleep stage classification result for the processed signal data by deploying a sleep stage classification model having a currently validated highest performance;
a training module configured to iteratively conduct a search on a hyperparameter of the deployed sleep stage classification model and to validate the deployed sleep stage classification model based on the iterative search result; and
a database configured to store validation data acquired by validating the sleep stage classification model,
wherein the training module is configured to compare the stored validation data and a performance of a sleep stage classification model being currently deployed and to control the service module to deploy a sleep stage classification model having a higher performance than the performance of the currently deployed sleep stage classification model,
wherein the signal data is collected in an EDF from a plurality of different equipments,
wherein the signal data processor comprises a data correction processor configured to process a correction or an interpolation of the signal data for an omitted portion in response to an omission of the portion of the signal data, and
wherein the data correction processor is configured to measure a differential value of the signal data as a secondary change rate of the signal data, to blank-process a portion in which the secondary change rate is largest in the signal data, and to restore a signal of a defect portion by performing a primary interpolation on the blank-processed portion.

2. The data processing apparatus of claim 1, wherein the signal data is collected in a European data format (EDF) from a plurality of different equipments, and
the signal data processor comprises a data selector configured to unify a key value for accessing the signal data, a sampling frequency value, a type of the signal data, and a format of the signal data.

3. The data processing apparatus of claim 2, wherein the data selector is configured to manage the signal data using a unified sampling frequency by defining a different sampling frequency for each piece of the collected signal data as a value of two or more folds of a Nyquist frequency through at least one of up-sampling and down-sampling.

4. The data processing apparatus of claim 2, wherein the data selector is configured to collect the signal data using predefined channels, and to unify a number of signal channels for each polysomnography equipment and inspection type through channel addition or channel duplication for the predefined channels.

5. The data processing apparatus of claim 4, wherein the data selector is configured to, when an omission of the signal data occurs in a channel for collecting the EEG signal or a channel for collecting the EOG signal or when the signal data is excluded from the polysomnography, replace the EEG signal with another EEG signal present at a most adjacent position among the same ground signals, and to replace the EOG signal with a signal present at a position opposite to a position of an omitted signal.

6. An operation method of a data processing apparatus, the method comprising:
collecting signal data detected through polysomnography;
extracting feature data by analyzing a feature of each of an electroencephalographic (EEG) signal, an electro-oculographic (EOG) signal, and an electromyographic (EMG) signal with respect to the signal data;
transforming the extracted feature data to an epoch unit of time series data to input the extracted feature data to a pre-generated sleep stage classification model; and
inputting the processed signal data to the pre-generated sleep stage classification model and classifying a sleep stage corresponding to the signal data,
wherein the data processing apparatus includes a sleep stage classification model generator configured to generate the sleep stage classification model,
wherein the operation method comprises:
defining, by the sleep stage classification model generator, statistical sequence data of each sleep stage for inferring the sleep stage classification model by sequentially applying an input layer, a one-dimensional (1D) convolution layer, a long short-term memory (LSTM) layer, and a softmax layer;

performing, by the sleep stage classification model generator, a training by processing all of the sets of the detected signal data through a processor, by caching the processed signal data for each set in a storage device, and by loading the cached signal data for each set; and comparing, by the sleep stage classification model generator, a test set acquired from a distribution of collected samples and a result of the inferred sleep stage classification model, wherein the data processing apparatus further comprises an inference model performance improver including a service module, a training module and a database, wherein the operation method further comprises:

outputting, by the service module, a sleep stage classification result for the processed signal data by deploying a sleep stage classification model having a currently validated highest performance, iteratively conducting, by the training module, a search on a hyperparameter of the deployed sleep stage classification model and validating, by the training module, the deployed sleep stage classification model based on the iterative search result, storing validation data acquired by validating the deployed sleep stage classification model in the database, and comparing, by the training module, the stored validation data and a performance of a sleep stage classification model being currently deployed and controlling, by the training module, the service module to deploy a sleep stage classification model having a higher performance than the performance of the currently deployed sleep stage classification model, wherein the collecting of the signal data comprises processing a correction or an interpolation of the signal data for an omitted portion in response to an omission of the portion of the signal data, and wherein the processing of the correction or the interpolation comprises:

measuring a differential value of the signal data as a secondary change rate of the signal data;

blank-processing a portion in which the secondary change rate is largest; and restoring a signal of a defect portion by performing a primary interpolation on the blank-processed portion.

7. The method of claim 6, wherein, when an omission of the signal data occurs in a channel for collecting the EEG signal or a channel for collecting the EOG signal or when the signal data is excluded from the polysomnography, the collecting of the signal data comprises replacing the EEG signal with another EEG signal present at a most adjacent position among the same ground signals and replacing the EOG signal with a signal present at a position opposite to a position of an omitted signal.

* * * * *